United States Patent
Graf

(10) Patent No.: US 8,098,378 B2
(45) Date of Patent: Jan. 17, 2012

(54) ENERGY-EFFICIENT OPERATING METHOD FOR A GAS SENSOR

(75) Inventor: Alexander Graf, Friedrichshafen (DE)

(73) Assignee: Robert Bosch GmbH, Stuttgart (DE)

( * ) Notice: Subject to any disclaimer, the term of this patent is extended or adjusted under 35 U.S.C. 154(b) by 231 days.

(21) Appl. No.: 12/496,972

(22) Filed: Jul. 2, 2009

(65) Prior Publication Data

US 2010/0007890 A1 Jan. 14, 2010

(30) Foreign Application Priority Data

Jul. 14, 2008 (DE) .......................... 10 2008 040 382

(51) Int. Cl.
*G01N 21/00* (2006.01)

(52) U.S. Cl. ........................................ 356/437; 356/432

(58) Field of Classification Search .......... 356/432–437; 250/343, 336.1, 338.1, 504 R, 493.1, 339.13, 250/339.06, 339.12; 73/19.01, 23.2; 219/553

See application file for complete search history.

(56) References Cited

U.S. PATENT DOCUMENTS 3,740,555 A * 6/1973 Schaefer ........................ 250/345
4,859,859 A * 8/1989 Knodle et al. ............. 250/504 R

FOREIGN PATENT DOCUMENTS

DE        199 22 590        9/2000

* cited by examiner

*Primary Examiner* — Gregory J Toatley
*Assistant Examiner* — Tri T Ton
(74) *Attorney, Agent, or Firm* — Kenyon & Kenyon LLP

(57) ABSTRACT

Energy-efficient operating method for a gas sensor. In a method for determining a gas concentration with the aid of a gas sensor having a radiation source, the radiation source
 is operated using a first electric power in a first operating mode, and
 is operated at a second electric power in a second operating mode,
 the second electric power being greater than the first electric power.

12 Claims, 2 Drawing Sheets

ENERGY-EFFICIENT OPERATING METHOD FOR A GAS SENSOR

BACKGROUND INFORMATION

An infrared gas sensor, which has an energy-supply device for operating at least one radiation source using current or voltage pulses, is described in German Patent No. DE 199 22 590. The gas sensor has at least one measuring chamber disposed in the optical path, and at least one wavelength-selective element and at least one detector element emitting an electric measuring signal. Furthermore, a switching device for regulating the pulse duration of the current or voltage pulses is provided. The switching device has means for setting the pulse duration, and the switching is implemented such that the current or voltage pulse is deactivated in such a way that the pulse duration is smaller than required to achieve the maximum of the at least one measuring signal of the at least one detector element.

SUMMARY OF THE INVENTION

The present invention relates to a method for determining a gas concentration with the aid of a gas sensor having a radiation source, in which the radiation source
  is operated using a first electric power or first electric voltage or first electric current in a first operating mode, and
  is operated using a second electric power or second electric voltage or second electric current in a second operating mode,
  the second electric power being greater than the first electric power, or the second electric voltage being greater than the first electric voltage, or the second electric current being greater than the first electric current. This makes it possible to choose between an energy-saving first operating mode and a more energy-intensive second operating mode, depending on the requirements.

One advantageous refinement of the present invention is characterized in that
  the radiation source is operated using the first electric power if the determined gas concentration is below a specified threshold value, and
  the radiation source is operated using the second electric power if the determined gas concentration exceeds the specified threshold value.

In other words, at a low measured gas concentration, the gas sensor is able to be operated in an energy-saving mode.

One advantageous refinement of the present invention is characterized in that the radiation source is an infrared radiation source.

One advantageous refinement of the present invention is characterized in that the gas sensor is used in a motor vehicle and, depending on the operating mode of the radiation source and/or the determined gas concentration,
  an air-recirculation regulation and/or a fresh-air regulation is implemented in the motor vehicle, and/or
  the driver is informed, for instance in a visual, acoustic or haptic manner.

One advantageous refinement of the present invention is characterized in that the measuring precision of the gas sensor is lower in the first operating mode than in the second operating mode. Because the first operating mode is used only at low gas concentrations, the measuring precision does not play a decisive role there, and a lower measuring precision is acceptable.

One advantageous refinement of the present invention is characterized in that the gas concentration to be determined is the carbon dioxide concentration. In the case of air-conditioning systems that operate on the basis of carbon dioxide, the determination of the carbon dioxide concentration in motor vehicles is very important in order to detect leaks in a timely manner.

One advantageous refinement of the present invention is characterized in that the radiation source is operated using a pulsed control.

One advantageous refinement of the present invention is characterized in that the radiation source is operated at the second electric power also when the temporal change of the determined gas concentration exceeds a predefined threshold value. In this way the sensor is already able to switch over into the more precise measuring mode when an exceeding of the threshold value appears imminent due to the high gradient.

Furthermore, the present invention provides a control device for a gas sensor, having means designed to implement the methods described above.

The advantageous refinements of the method according to the present invention manifest themselves also as advantageous embodiments of the device according to the present invention, and vice versa.

DETAILED DESCRIPTION

Known gas sensors are operated using a constant measuring cycle. The duration of the ON pulses for the radiation source and the output of the radiation source are constant. New uses of infrared gas sensors in the automotive field require the operation of the sensor even when the engine is turned off. As a result, the present invention includes a new operating method for an IR gas sensor, which makes it possible to reduce the energy consumption considerably on the basis of an intelligent sensor control. The energy consumption of the sensor is able to be reduced in that a switchover between two different operating modes takes place, the operating modes having a higher or lower energy consumption for precise or less precise measurements, respectively, as a function of the required measuring accuracy. The energy consumption is essentially defined by the intensity of the IR emitter.

The present invention utilizes the fact that the full measuring accuracy is not required across the entire operating time. This makes it possible to define two operating modes.

Figure 1:
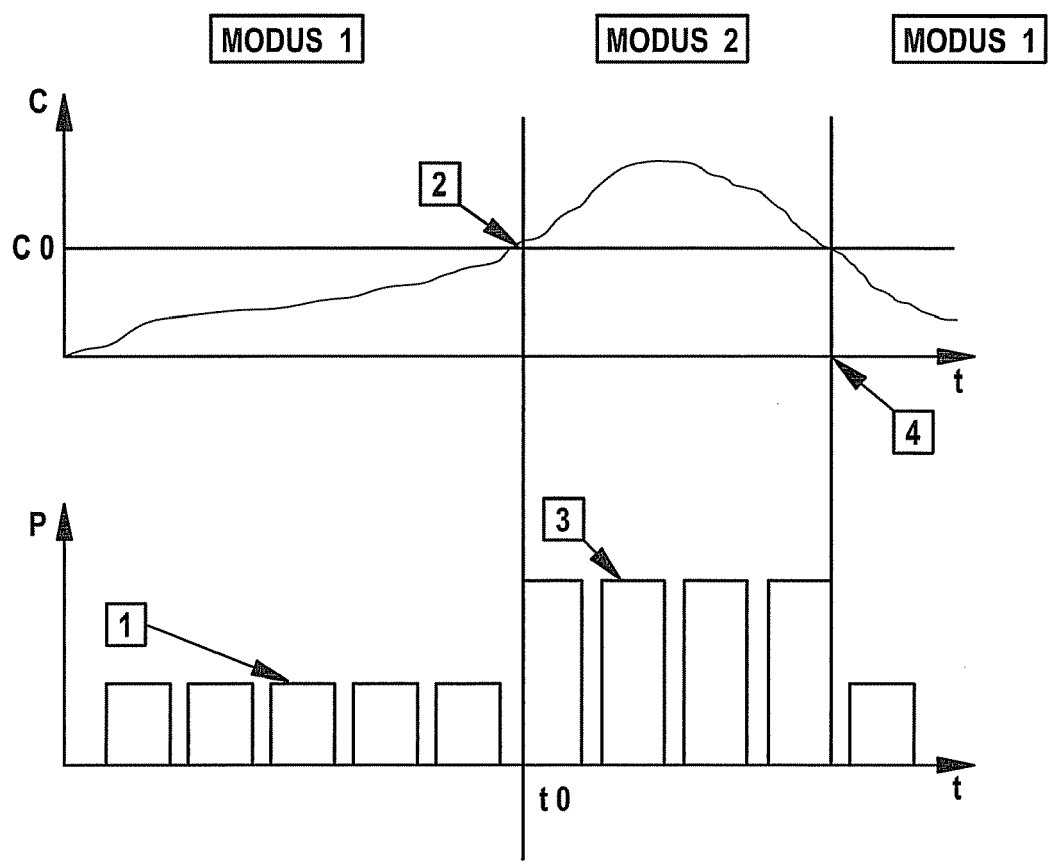
FIG. 1 shows time characteristics of the determined gas concentration and the control power of the radiation source.

In the basic state, hereinafter also denoted by mode 1, the sensor measures continuously, with low precision. Because of the low output, denoted by 1 in FIG. 1, that is required for the IR source in this state, the average energy consumption of the sensor is able to be lowered considerably, which allows for longer operating times in battery operation. Nevertheless, the measuring precision in this state is sufficient to implement a threshold value detection. To this end, it must be detected when the concentration of the target gas rises above a specific concentration threshold. This concentration threshold is denoted by C0 in the upper diagram of FIG. 1 and is reached at instant t0 (cf. marking "2" in FIG. 1). In this diagram time t is plotted in the abscissa direction, concentration C of the target gas is plotted in the ordinate direction. The target gas may be carbon dioxide, for example. Alternatively, chronological monitoring of the gas concentration for the occurrence of characteristic patterns may also take place. If the concentration rises above the threshold value or if characteristic patterns can be discerned in the concentration characteristic, then the sensor automatically switches into mode 2, which is shown in FIG. 1. Operating mode 2 is characterized by an increased intensity of the radiation source, which is marked by 3 in the lower diagram of FIG. 3.

Time t is plotted in the abscissa direction in this diagram, and the output, denoted by p, of the IR radiation source is plotted in the ordinate direction. At time t0, the concentration exceeds the threshold denoted by 2; starting at this time, the source is triggered using a higher current intensity or voltage. In more precise mode 2, the concentration is able to be determined accurately, and appropriate counter measures may be initiated. After the critical situation has abated, denoted by 4 in FIG. 1, it is possible to switch back into operating mode 1. Characteristic patterns are to be understood as high temporal gradients of the concentration, for instance. This allows the sensor to switch into the second operating mode even before reaching the threshold value concentrations.

Figure 2:
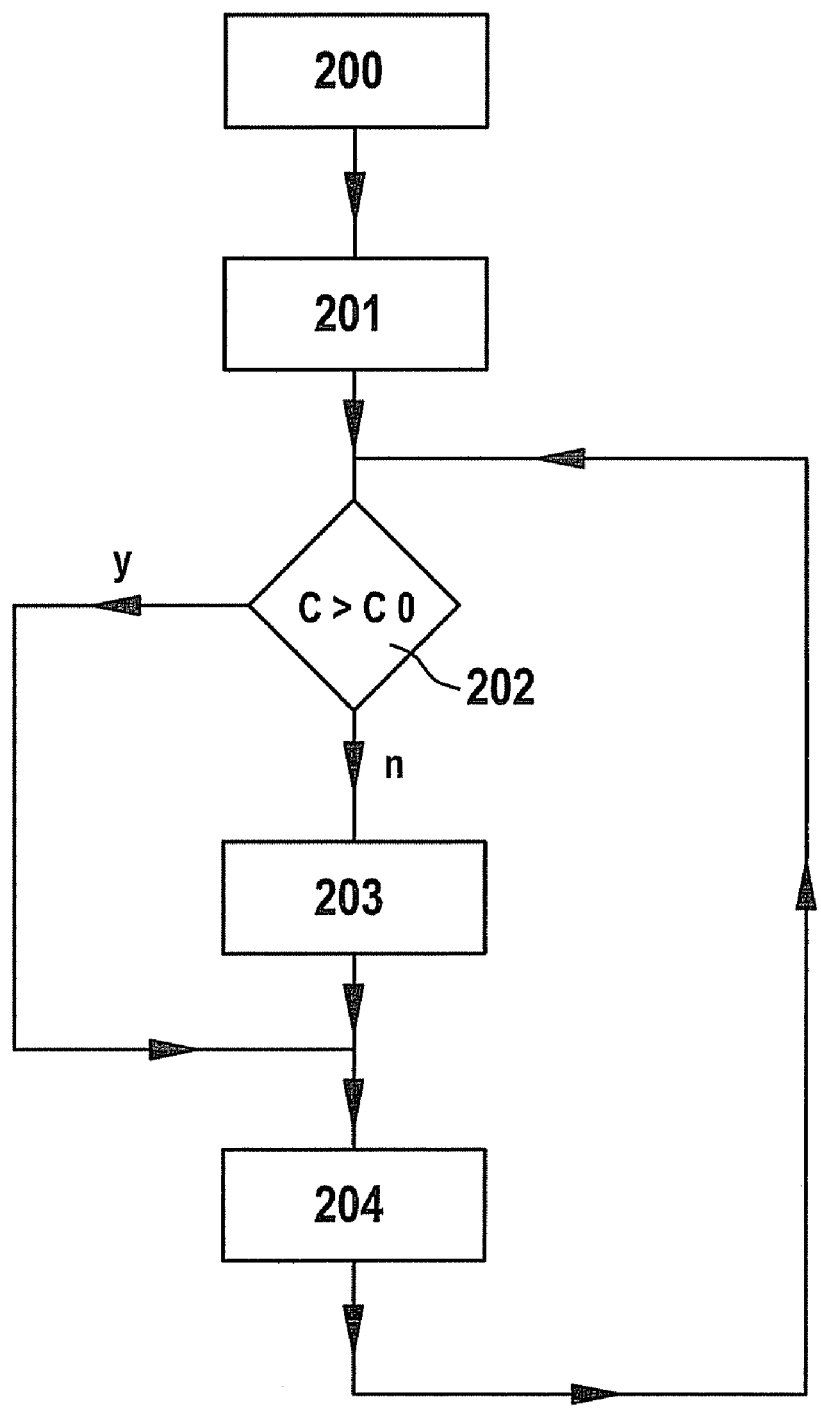
FIG. 2 shows a development of the sequence of the method according to the present invention.

The sequence of a specific embodiment of the method according to the present invention is shown in FIG. 2. Following the start in block 200, concentration C of the gas to be detected is measured in block 201, the radiation source being in the second operating mode. Then, in block 202 it is queried whether concentration C exceeds threshold value C0. If C<C0, then the radiation source is switched into the first operating mode in subsequent block 203, and it is then proceeded to block 204. On the other hand, if C>C0 in block 202, then it is directly proceeded to block 204. In block 204, a fresh-air regulation or an air-recirculation regulation takes place in a motor vehicle as a function of the determined gas concentration, or an item of driver information is output. It is then branched back to the input of block 202.

A detector based on a thermopile, for example, may be used as a detection element for the infrared sensor. The thermopile is able to be produced using surface-micromechanical technology, for example.

What is claimed is:

1. A method for determining a gas concentration with the aid of a gas sensor having a radiation source, the method comprising:
   operating the radiation source of the gas sensor using a first electric power in a first operating mode; and
   operating the radiation source of the gas sensor using a second electric power in a second operating mode, the second electric power being greater than the first electric power,
   wherein the radiation source is operated using the first electric power if the determined gas connection is below a specified threshold value, and the radiation source is operated using the second electric power if the determined gas concentration exceeds the specified threshold value.

2. The method according to claim 1, wherein the gas sensor is used in a motor vehicle, and at least one of an air recirculation regulation and a fresh air regulation is implemented in the motor vehicle as a function of the detected gas concentration.

3. The method according to claim 1, wherein the radiation source is an infrared radiation source.

4. A method for determining a gas concentration with the aid of a gas sensor having a radiation source, the method comprising:
   operating the radiation source of the gas sensor using a first electric power in a first operating mode; and
   operating the radiation source of the gas sensor using a second electric power in a second operating mode, the second electric power being greater that the first electric power,
   wherein the gas sensor is used in a motor vehicle, and at least one of a fresh air regulation and an air recirculation regulation is implemented in the motor vehicle as a function of an operating mode.

5. A method for determining a gas concentration with the aid of a gas sensor having a radiation source, the method comprising:
   operating the radiation source of the gas sensor using a first electric power in a first operating mode; and
   operating the radiation source of the gas sensor using a second electric power in a second operating mode, the second electric power being greater than the first electric power,
   wherein the gas sensor is used in a motor vehicle, and at least one of an air recirculation regulation and a fresh air regulation is implemented in the motor vehicle as a function of the detected gas concentration.

6. The method according to claim 1, wherein the gas sensor is used in a motor vehicle, and information is output to a driver as a function of the detected gas concentration.

7. The method according to claim 1, wherein, in the first operating mode, the gas sensor has lower measuring accuracy than in the second operating mode.

8. The method according to claim 1, wherein the gas concentration to be determined is a carbon dioxide concentration.

9. The method according to claim 1, wherein the radiation source is operated using a pulsed control.

10. The method according to claim 1, wherein the radiation source is operated at the second electric power also when a temporal change of the determined gas concentration exceeds a predefined threshold value.

11. A control device for a gas sensor for determining a gas concentration, the gas sensor having a radiation source, the control device comprising:
   means for operating the radiation source of the gas sensor using a first electric power in a first operating mode; and
   means for operating the radiation source of the gas sensor using a second electric power in a second operating mode, the second electric power being greater than the first electric power,
   wherein the radiation source is operated using the first electric power if the determined gas concentration is below a specified threshold value, and the radiation source is operated using the second electric power if the determined gas concentration exceeds the specified threshold value.

12. The method according to claim 1, wherein the gas sensor is used in a motor vehicle, and at least one of a fresh air regulation and an air recirculation regulation is implemented in the motor vehicle as a function of an operating mode.

* * * * *